(12) United States Patent
Beeckler et al.

(10) Patent No.: US 11,553,831 B2
(45) Date of Patent: Jan. 17, 2023

(54) MALLEABLE SUCTION DEVICE

(71) Applicant: BIOSENSE WEBSTER (ISRAEL) LTD., Yokneam (IL)

(72) Inventors: Christopher Thomas Beeckler, Brea, CA (US); Kevin Mark Okarski, Monrovia, CA (US); Assaf Govari, Haifa (IL); Vadim Gliner, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 551 days.

(21) Appl. No.: 16/552,132

(22) Filed: Aug. 27, 2019

(65) Prior Publication Data
US 2020/0107704 A1 Apr. 9, 2020

Related U.S. Application Data (60) Provisional application No. 62/741,402, filed on Oct. 4, 2018.

(51) Int. Cl.
*A61B 1/00* (2006.01)
*A61B 1/233* (2006.01)
(Continued)

(52) U.S. Cl.
CPC ...... *A61B 1/00154* (2013.01); *A61B 1/00018* (2013.01); *A61B 1/0055* (2013.01);
(Continued)

(58) Field of Classification Search
CPC . A61B 34/20; A61B 1/00018; A61B 1/00097; A61B 1/00154; A61B 1/0055;
(Continued)

(56) References Cited

U.S. PATENT DOCUMENTS 6,253,770 B1 * 7/2001 Acker ............... A61M 25/0127
128/899
6,593,884 B1 * 7/2003 Gilboa ............... A61B 5/062
342/450
(Continued)

FOREIGN PATENT DOCUMENTS

EP 2532300 12/2012

OTHER PUBLICATIONS

International Search Report and Written Opinion dated Nov. 6, 2019 from corresponding PCT/IB2019/058077 application.

*Primary Examiner* — Aaron B Fairchild
(74) *Attorney, Agent, or Firm* — Frost Brown Todd LLP (57) ABSTRACT

A surgical tool, consisting of a handle and a flexible insertion tube, having a proximal end coupled to the handle and a distal end configured to be inserted into an orifice of a living subject. The tool has an inner tube, which is bendable without breaking over a range of angles in response to a bending force, and which retains the bent shape after the bending force has been removed. The inner tube is located within the insertion tube. A flexible tubing defines a lumen and is contained within the inner tube. A tool working tip is configured to contact tissue in the subject and to mate with a distal termination of the inner tube. A rigid outer tube grips outer surfaces of the working tip and of the inner tube so as to maintain an opening of the working tip in communication with the flexible tubing lumen.

20 Claims, 5 Drawing Sheets

(51) Int. Cl.
*A61B 1/01* (2006.01)
*A61B 1/005* (2006.01)
*A61B 34/20* (2016.01)
*A61B 1/05* (2006.01)
*A61B 17/24* (2006.01)
*A61B 1/015* (2006.01)
*A61B 17/00* (2006.01)
*A61M 1/00* (2006.01)

(52) U.S. Cl.
CPC ............ *A61B 1/00097* (2022.02); *A61B 1/01* (2013.01); *A61B 1/015* (2013.01); *A61B 1/05* (2013.01); *A61B 1/233* (2013.01); *A61B 17/24* (2013.01); *A61B 34/20* (2016.02); *A61B 2017/00862* (2013.01); *A61B 2017/00946* (2013.01); *A61B 2034/2051* (2016.02); *A61B 2217/005* (2013.01); *A61M 1/84* (2021.05)

(58) Field of Classification Search
CPC .. A61B 1/01; A61B 1/015; A61B 1/05; A61B 1/233; A61B 1/0008; A61B 1/00135
See application file for complete search history.

(56) References Cited

U.S. PATENT DOCUMENTS

| | | |
|---|---|---|
| 9,226,800 B2 | 1/2016 | Burg et al. |
| 2005/0165275 A1* | 7/2005 | Von Felten ........ G02B 23/2476 600/140 |
| 2007/0157937 A1* | 7/2007 | Mikkaichi ............. A61B 90/39 128/898 |
| 2009/0093680 A1* | 4/2009 | Tsutsumi ............ A61B 1/0008 600/140 |
| 2011/0270081 A1* | 11/2011 | Burg ..................... A61B 34/20 600/424 |
| 2014/0187894 A1 | 7/2014 | Bui et al. |
| 2014/0206985 A1* | 7/2014 | Kariv .................... A61B 5/065 600/424 |
| 2018/0214138 A9 | 8/2018 | Prisco et al. |
| 2019/0134364 A1* | 5/2019 | Hanson ................. A61B 17/24 |
| 2019/0224452 A1* | 7/2019 | Jenkins .............. A61M 3/0279 |

* cited by examiner

# MALLEABLE SUCTION DEVICE

CROSS-REFERENCE TO RELATED APPLICATIONS

This application claims the benefit of U.S. Provisional Patent Application 62/741,402 filed Oct. 4, 2018, which is incorporated herein by reference.

FIELD OF THE INVENTION

This invention relates generally to surgical tools, and specifically to a rigid surgical tool having a shape which is adjustable.

BACKGROUND OF THE INVENTION

The nasal sinuses are complicated three-dimensional structures that vary from person to person, so that access to a particular sinus, and to a selected region of the sinus, may require a rigid tool having a very specific shape to achieve such access. Furthermore, an optimal shape of the tool may only be apparent after inspection of a computerized tomography (CT) image of the patient. Surgical tools for a sinus, such as endoscopes, graspers, and/or suction devices, are produced in a variety of shapes which are typically available to the physician. Thus, an operating ENT physician is able to choose the particular shape that is most suited to a specific task within the sinus. However, even though there may be a variety of tool shapes available to the physician, none of these shapes may be optimal. In addition, the provision of multiple rigid tools (having different shapes) to a physician is costly.

U.S. Pat. No. 9,226,800, to Burg, et al., describes a malleable surgical instrument which can be bent from a first configuration to a second bent configuration and can maintain the bent configuration.

SUMMARY OF THE INVENTION

An embodiment of the present invention provides a surgical tool, including:

a handle;

a flexible insertion tube, having a proximal end coupled to the handle and a distal end configured to be inserted into an orifice of a body of a living subject;

an inner tube, which is bendable without breaking over a range of angles from 0 to 120 degrees in response to a bending force, and which is configured, after being bent into a bent shape, to retain the bent shape after the bending force has been removed, the inner tube being located within the insertion tube and having a distal termination in proximity to the distal end of the insertion tube;

a flexible tubing, which defines a lumen and which is contained within the inner tube;

a working tip, which has an opening, and which is configured to contact tissue in the body and to mate with the distal termination of the inner tube; and a rigid outer tube, which grips respective outer surfaces of the working tip and of the inner tube so as to maintain the opening of the working tip in communication with the flexible tubing lumen.

Typically there is at least one magnetic sensor located in proximity to the working tip.

In a disclosed embodiment the at least one magnetic sensor includes a first coil having a first axis of symmetry and a second coil having a second axis of symmetry that comprises a component orthogonal to the first axis. The second axis of symmetry may make a non-orthogonal angle between 60° and 120° with the first axis.

In a further disclosed embodiment the at least one magnetic sensor is configured to generate a signal, indicative of a location and an orientation of the working tip within the body, in response to a magnetic field traversing the at least one magnetic sensor.

In a yet further disclosed embodiment the tool has cabling, connected to the at least one magnetic sensor and configured to transfer signals therefrom, the cabling being located between the inner tube and the flexible insertion tube.

In an alternative embodiment the flexible insertion tube at least partially covers the outer tube.

In a further alternative embodiment the inner tube is formed from bendable aluminum.

The tool may be operative as a suction tool.

In a yet further alternative embodiment the tool may include a camera positioned in the working tip and configured to image a section of the body external to the tip. The working tip may be formed as a rigid tubular element, and the camera may be located within the rigid tubular element.

There is further provided, according to an embodiment of the invention a method, including:

providing a handle;

forming a flexible insertion tube by reflowing a thermoplastic elastomer;

coupling a proximal end of the flexible insertion tube to the handle, the flexible insertion tube having a distal end configured to be inserted into an orifice of a body of a living subject;

locating an inner tube within the insertion tube, the inner tube being bendable without breaking over a range of angles from 0 to 120 degrees in response to a bending force, and being configured, after being bent into a bent shape, to retain the bent shape after the bending force has been removed, wherein the inner tube has a distal termination in proximity to the distal end of the insertion tube;

locating a flexible tubing within the inner tube, the flexible tubing defining a lumen;

mating a working tip, which is configured to contact tissue in the body and which has an opening, with the distal termination of the inner tube; and gripping respective outer surfaces of the working tip and of the inner tube with a rigid outer tube so as to maintain the opening of the working tip in communication with the flexible tubing lumen.

Typically, reflowing the elastomer includes placing a heat shrink tube over the elastomer, heating the heat shrink tube so as to cause the heat shrink tube to shrink and the elastomer to melt, and then removing the heat shrink tube.

The present disclosure will be more fully understood from the following detailed description of the embodiments thereof, taken together with the drawings, in which:

DETAILED DESCRIPTION OF EMBODIMENTS

Overview

In a medical procedure requiring access to an internal organ of a patient, such as a patient sinus, there are typically a plurality of tools available to a physician performing the procedure. The physician may choose the tool most suited for the access. However, having a multiplicity of tools available is expensive, and none of the tools may be exactly as desired by the physician.

Embodiments of the present invention overcome these problems by having a single rigid tool that the physician may bend into a desired shape. After bending, the tool is still rigid enough to be suitable for its intended use. In one embodiment the single rigid tool is a suction tool configured for use in a nasal sinus procedure.

In an embodiment of the invention the single rigid tool comprises a handle to which is coupled a flexible insertion tube. The flexible insertion tube acts as a protective cover for elements of the tool that the tube encloses. A proximal end of the tube is coupled to the handle, and a distal end of the tube is configured to be inserted into an orifice of a living subject.

An inner tube is located within the flexible insertion tube so that a distal termination of the inner tube is in proximity to the distal end of the flexible insertion tube. The inner tube defines an inner tube lumen, and the inner tube has the property of being malleable, so that it is bendable, in response to a bending force, without breaking. The inner tube may thus be bent in a range of angles. A further property of the inner tube is that it retains its bent shape after the bending force is removed.

The tool comprises a flexible tubing which defines a lumen and which is contained within the inner tube.

The tool also comprises a working tip that mates with the inner tube distal termination and which has an opening. The working tip, typically a suction tip if the rigid tool is a suction tool, is configured to contact tissue of the subject.

The tool further comprises a rigid outer tube, which grips outer surfaces of the working tip and of the inner tube so as to maintain the opening of the working tip in communication with the flexible tubing lumen.

Typically, the rigid tool comprises at least one magnetic sensor located in proximity to the working tip. The at least one sensor enables the location and orientation of the working tip to be tracked. In one embodiment the at least one sensor comprises a pair of sensor coils having axes of symmetry between 60° and 120° to each other.

DETAILED DESCRIPTION

In the following description, like elements in the drawings are identified by like numerals, and like elements are differentiated as necessary by appending a letter to the identifying numeral.

Figure 1:
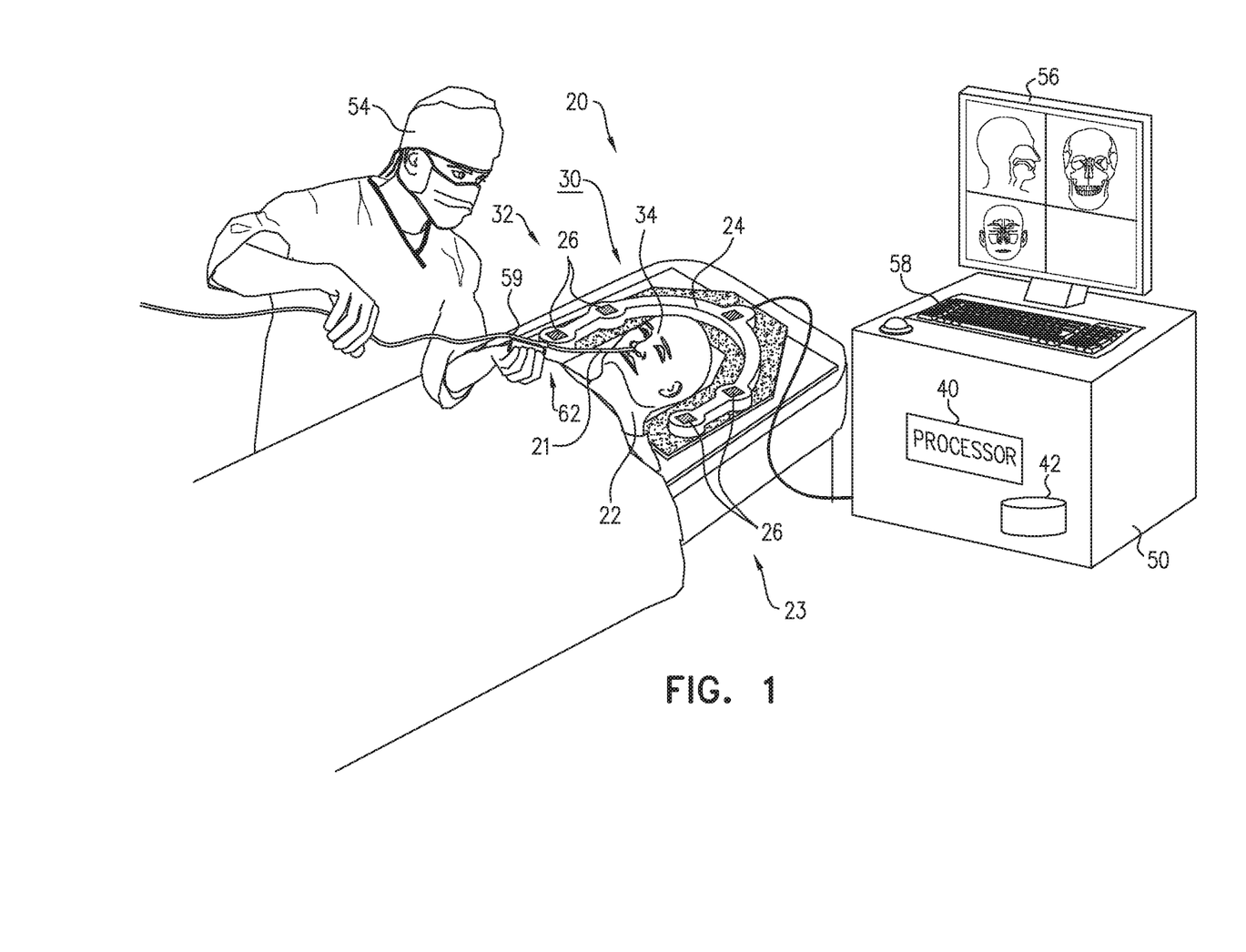
FIG. 1 is a schematic illustration of an ENT (ear, nose, and throat) system, according to an embodiment of the present invention.

Reference is now made to FIG. 1, which is a schematic illustration of an ENT (ear, nose, and throat) system 20, according to an embodiment of the present invention. System 20 is operated by a system processor 40 communicating with one or more memories 42. In the following description system 20 comprises a rigid surgical tool 21 which a physician 54 is assumed to use to perform a nasal sinus procedure on a patient 22, and, as is described in more detail below, the tool comprises a magnetic sensor 32 that is tracked during the procedure by a magnetic tracking system 23. For the tracking to be effective, in system 20 frames of reference of a CT (computerized tomography) image of patient 22 and of magnetic tracking system 23 are registered. While the CT image may typically comprise a magnetic resonance imaging (MRI) image or a fluoroscopic image, in the description herein the image is assumed to comprise, by way of example, a fluoroscopic CT image, Prior to and during the sinus procedure, a magnetic radiator assembly 24, comprised in the magnetic tracking system, is positioned beneath the patient's head. Assembly 24 comprises magnetic field radiators 26 which are fixed in position and which transmit alternating sinusoidal magnetic fields into a region 30 wherein the head of patient 22 is located. By way of example, radiators 26 of assembly 24 are arranged in an approximately horseshoe shape around the head of patient 22. However, alternate configurations for the radiators of assembly 24 to radiate into region 30 are also assumed to be comprised within the scope of the present invention.

Elements of system 20, including radiators 26, are controlled by system processor 40. Processor 40 may be mounted in a console 50, which comprises operating controls 58 that typically include a keypad and/or a pointing device such as a mouse or trackball. Console 50 connects to the radiators via a cable and/or wirelessly. Physician 54 uses operating controls 58 to interact with the processor while performing the ENT procedure using system 20. While performing the procedure, the processor may present results of the procedure on a screen 56.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 uses the software, inter alia, to operate magnetic radiators 26 of assembly 24. As stated above the radiators transmit sinusoidal alternating magnetic fields of different frequencies into region 30, including the head of patient 22, and the fields from the radiators induce signals in sensor 32. The signals, and/or data derived from the signals, may be transmitted by wire and/or wirelessly to the processor which analyzes the received data and/or signals to derive location and orientation values, measured with respect to a frame of reference defined by the assembly, for the sensors.

In the description herein rigid surgical tool 21 is assumed to be a suction device, used for permitting drainage of fluid through a lumen of the device. However, the description may be adapted, mutatis mutandis, for other types of surgical tools, such as an endoscope or a grasper, and all such tools are assumed to be comprised within the scope of the present invention.

Figure 2A:
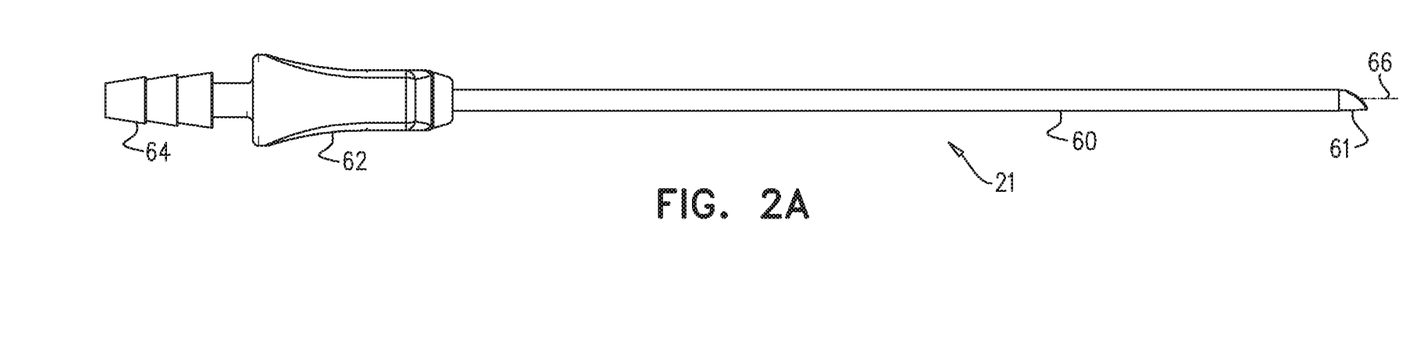
FIGS. 2A and 2B are schematic diagrams of a rigid tool in an unbent state, according to an embodiment of the present invention.
Figure 2B:
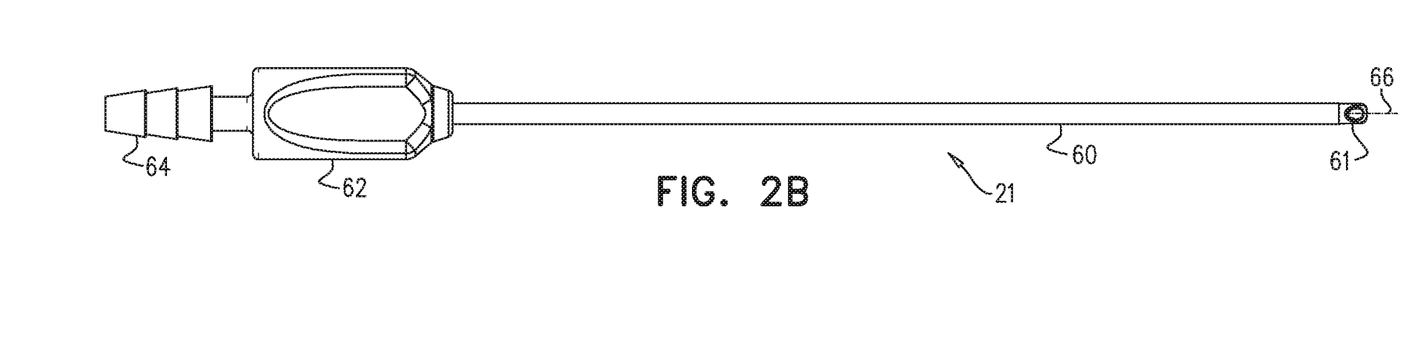
Figure 3A:
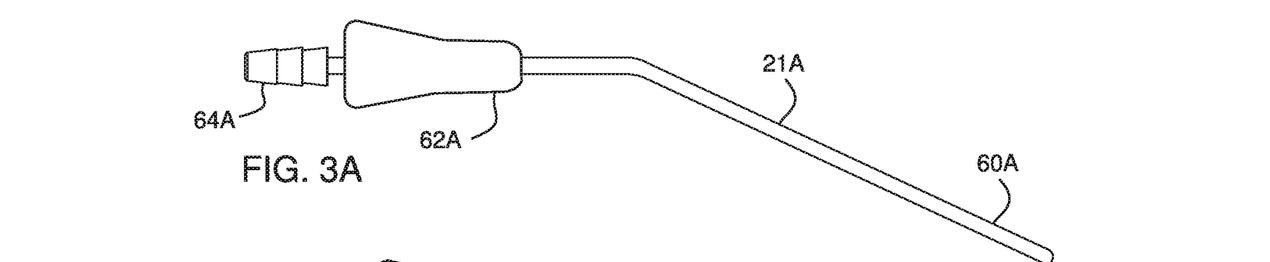
FIGS. 3A, 3B, 3C, and 3D are schematic diagrams of the rigid tool in exemplary bent states, according to an embodiment of the present invention.
Figure 3B:
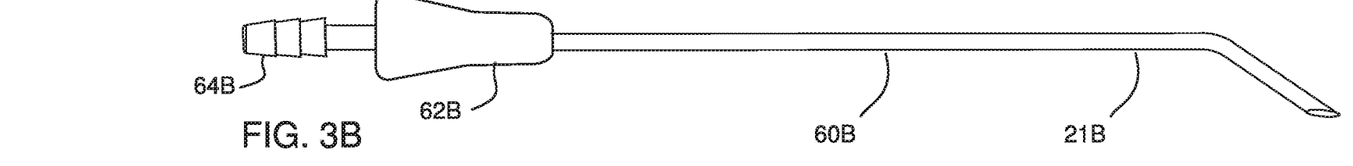
Figure 3C:
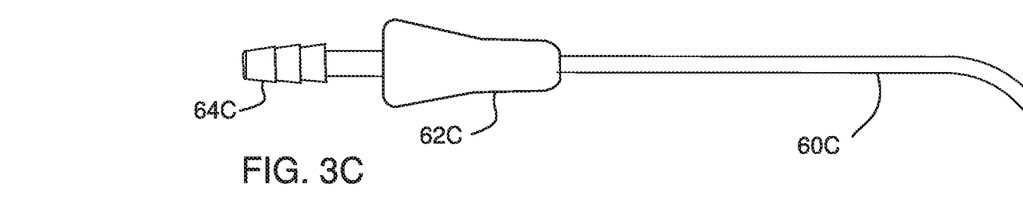
Figure 3D:
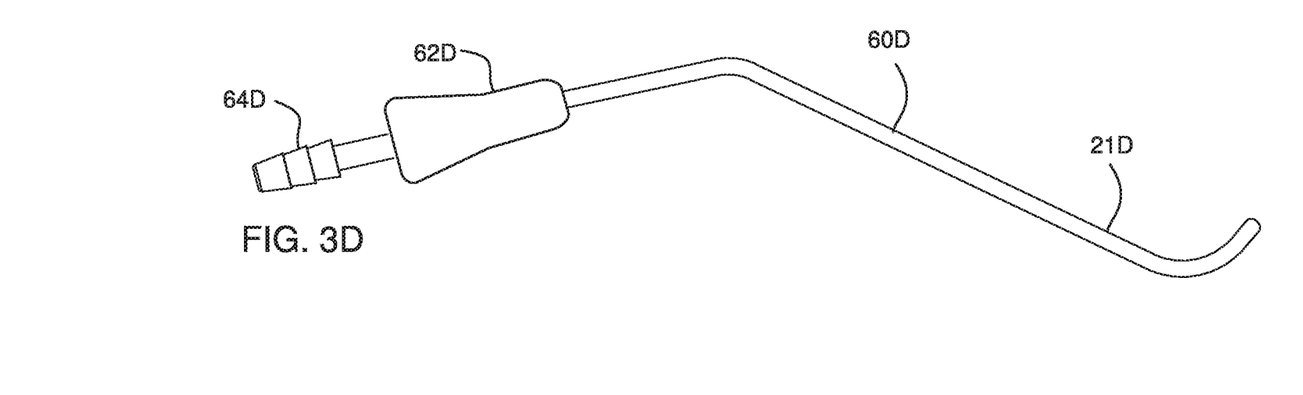

FIGS. 2A and 2B are schematic diagrams of rigid tool 21 in an unbent state, and FIGS. 3A, 3B, 3C, and 3D are schematic diagrams of the rigid tool in exemplary bent states, according to an embodiment of the present invention. FIG. 2A illustrates a top view of tool 21, and FIG. 2B illustrates a side view of the tool. Tool 21 comprises a bendable tubular member 60 which in its unbent form defines a central axis 66. Member 60 has a distal end 61, and the member and its distal end are both described in more detail below. At its proximal end bendable tubular member 60 is connected to a handle 62. Handle 62 comprises a coupling 64, enabling tubing 59 (not shown in FIGS. 2A and 2B, but shown schematically in FIG. 1) to be connected to the handle for the purpose of receiving drained fluid from member 60 when suction is applied. In some embodiments handle 62 may incorporate a control allowing the physician to control the suction through member 60.

FIGS. 3A, 3B, 3C, and 3D respectively schematically illustrate different examples of tool 21: tools 21A, 21B, 21C, and 21D, each formed by bending member 60 from its unbent state. Thus, tools 21A, 21B, 21C, and 21D comprise substantially similar couplings 64A, 64B, 64C, and 64D, and substantially similar handles 62A, 62B, 62C, and 62D. The tools each have different bent members 60A, 60B, 60C, and 60D.

Figure 4A:
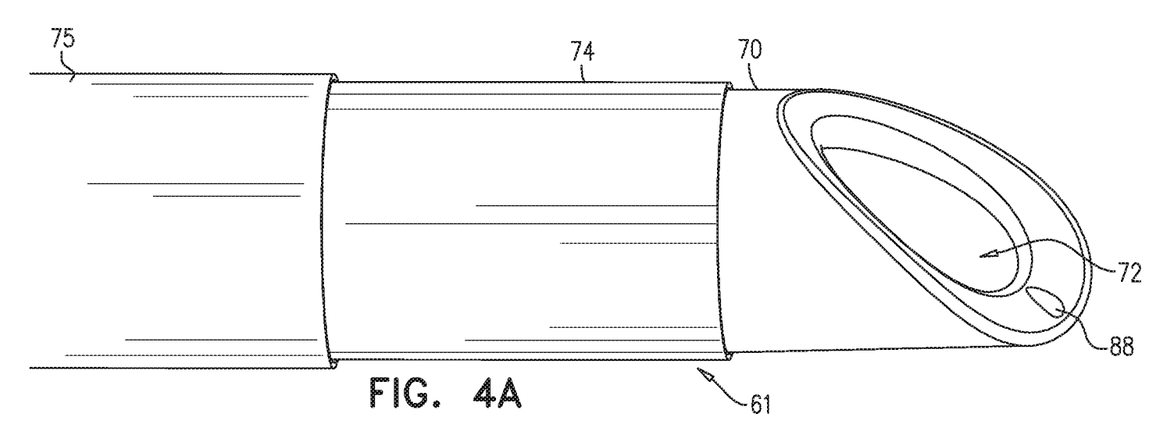
FIGS. 4A and 4B are schematic diagrams illustrating the structure of the rigid tool, according to an embodiment of the present invention.
Figure 4B:
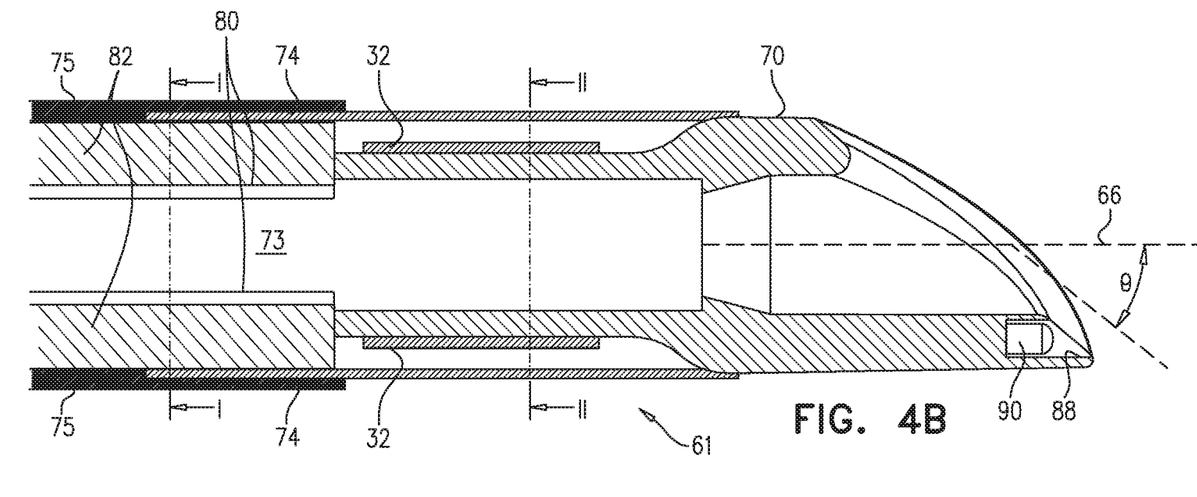
Figure 5A:
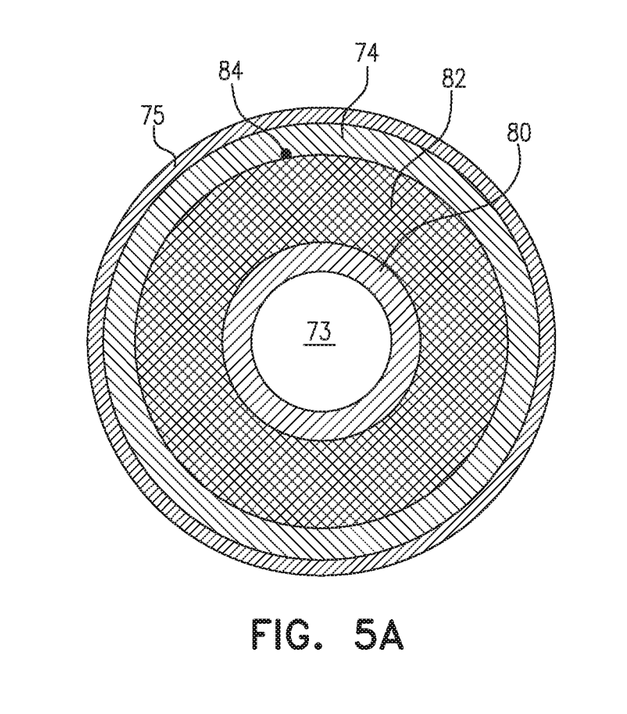
FIGS. 5A and 5B are schematic cross-sections of portions of the tool, according to an embodiment of the present invention.
Figure 5B:
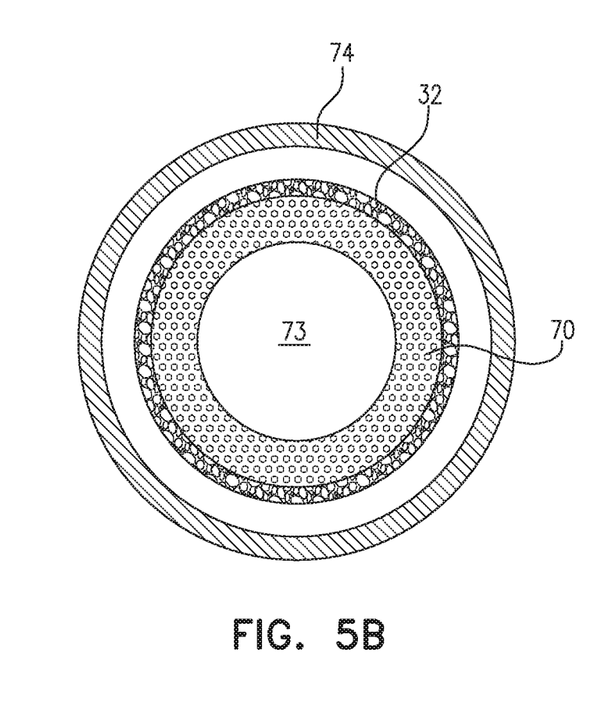

FIGS. 4A and 4B are schematic diagrams illustrating the structure of tool 21, and FIGS. 5A and 5B are schematic cross-sections of portions of the tool, according to an embodiment of the present invention. FIG. 4A is an external view of distal end 61, and FIG. 4B is a partially cut-away view of the distal end showing its internal elements. FIG. 5A is a cross-section of a proximal part of distal end 61, taken along a line I-I, and FIG. 5B is a cross-section of a central part of the distal end, taken along a line II-II.

Distal end 61 terminates in a working tip 70, also herein termed a suction tip, having an opening 72 leading to a lumen of member 60. The suction tip typically makes a non-orthogonal angle θ with central axis 66 of member 60, and in one embodiment angle θ is approximately 40°. Suction tip 70 is typically formed from a rigid biocompatible plastic such as PEEK (polyether ether ketone), polycarbonate, ABS (acrylonitrile-butadiene-styrene), polyamide, or UHMWPE (Ultra-high-molecular-weight polyethylene). In some embodiments the biocompatible plastic may be reinforced for added strength by adding glass or carbon fiber. In some embodiments θ may be 90°, creating a rotationally symmetric suction tip.

Suction tip 70 is held in place by a rigid tube 74, typically an extrusion and also referred to herein as extrusion 74, which in one embodiment is a rigid biocompatible plastic such as PEEK.

Extrusion 74 couples suction tip 70 to a bendable inner tube 82 by gripping outer surfaces of the suction tip and of the bendable inner tube, so that a proximal end of the suction tip contacts a distal end of the bendable inner tube, and so that opening 72 of the suction tip is in communication with a lumen 73 within the bendable inner tube. Lumen 73 is also referred to below. Bendable inner tube 82 is typically formed from bendable aluminum, and properties of the bendable inner tube are described below.

Bendable inner tube 82 is covered by a flexible insertion tube 75. In one embodiment insertion tube 75 is formed from a thermoplastic elastomer such as polyether block amide (PEBA), and the insertion tube may be formed by reflowing the elastomer on top of the inner tube. Reflowing may be accomplished by placing a loose fit extrusion of the thermoplastic elastomer over inner tube 82, placing a heat shrink tube over the extrusion, bringing the assembly up to a sufficient temperature to cause the heat shrink tube to shrink and the thermoplastic elastomer to melt, and allowing the assembly to cool so as to form insertion tube 75. Once the assembly is cool the heat shrink tube is removed.

In some embodiments flexible insertion tube 75 also covers some or all of extrusion 74. Tube 75 covers all of inner tube 82, is coupled to handle 62, and acts as a protective cover for member 60. Tube 75 also serves to cover and protect cabling 84 (described in more detail below) on the outside of bendable inner tube 82.

At its proximal end suction tip 70 is tubular, and in one embodiment magnetic sensor 32 is wound over an external surface of the tubular proximal end. Thus, in addition to acting as a rigid connector that grips and joins tip 70 to bendable inner tube 82, extrusion 74 acts to shield and isolate sensor 32 from the external surroundings. Between extrusion 74 and coil 32 there may be retaining material, such as a polyurethane adhesive or an epoxy. Signals from sensor 32 are transferred to handle 62, and from the handle to processor 40 (FIG. 1), via cabling 84. Cabling 84 (shown schematically as a cross-section in FIG. 5A) is wound spirally on the outer surface of bendable inner tube 82.

A flexible tubing 80, which extends the length of member 60, is located within bendable inner tube 82 from the tube distal end up to handle 62. In one embodiment tubing 80 is formed from a polyimide. Tubing 80 defines lumen 73, and the lumen of the tubing mates and communicates with opening 72 of the suction tip. Tubing 80 may also contain braiding to allow the tubing to take smaller radiused bends than would otherwise be possible without kinking.

In an alternate embodiment, tubing 80 may be in the form of a thin PTFE coating which lines the inner surface of tube 82.

In one embodiment sensor 32 is one single axis sensor (SAS) coil, typically formed as a planar spiral on a flexible printed circuit board. In an alternative embodiment, sensor 32 comprises two SAS planar spiral coils, typically formed as rectangular spirals, which have axes of symmetry that are not parallel to each other. While the two axes are optimally at 90° to each other, the axes may be between approximately 60° and approximately 120° to each other, so that one of the axes has a component that is orthogonal to the other axis. The inventors have found that even with axes at 60° or 120° from each other, the non-orthogonal coil still provides satisfactory signals, i.e., 87% of the signal if the coil was orthogonal, to processor 40, so enabling magnetic tracking system 23 to determine the position of distal end 61 in three linear dimensions, as well as the orientation of the distal end in three angular dimensions.

As described above, bendable inner tube 82 lies between flexible tubing 80 and flexible insertion tube 75. Inner tube 82 mates at its distal end with the proximal end of suction tip 70, and terminates at its proximal end with handle 62. Bendable inner tube 82 acts as a spine of member 60, so that while the member is bendable over substantially all of its length, except when exposed to a relatively high force the member is rigid. By configuring inner tube 82 to be bendable, a physician is able to shape member 60 as desired, and as exemplified in FIGS. 3A-3D.

In the disclosure and in the claims, an entity, such as inner tube 82, is assumed to be bendable if the entity can be bent, without breaking, over a range of angles from 0 to 120° in response to a bending force. A bendable entity further has the property that after being bent into a bent shape, it retains the bent shape after the bending force has been removed. Inner tube 82 is bendable, and so is also referred to herein as bendable tube 82.

In one embodiment bendable tube 82 is formed from a soft tempered aluminum alloy such as 3003.

In some embodiments the distal end of suction tip 70 has an opening 88 that is configured to fixedly accept a camera 90 in the opening. If necessary, the thickness of the suction tip may be increased to accommodate opening 88. Camera 90 provides an image of objects close to the suction tip, and the image may be presented to physician 54 on screen 56.

The image presented on screen 56 may be maintained in a fixed orientation, selected by the physician, regardless of any rotation of the suction tip. Processor 40 may be configured to maintain the fixed orientation, by using orientation measurements of the SASs referred to above to counteract any rotation of the suction tip. It will be understood that the processor may maintain the fixed orientation regardless of the shape taken by rigid tool 21 after bending.

In one embodiment, member 60 has a length of approximately 166 mm and an outside diameter of approximately 3.6 mm. Also sensor 32 has a length of approximately 3.2 mm, and the center of the sensor is approximately 8.3 mm from the distal tip of suction tip 70. However, it will be understood that these dimensions are by way of example, and other suitable dimensions may be determined without undue experimentation.

Returning to FIG. 1, in some embodiments registration of the CT image of patient 22 with magnetic tracking system 23 is performed using system 20 prior to the procedure referred to above. For the registration, a distal tip of suction tip 70 is touched at selected different regions of the skin of patient 22. The selected different regions are those, such as the nose tip of the patient or a point between the patient eyes, that are identifiable in the CT image. The signals induced in sensor 32 in response to the interaction with the magnetic fields produced by assembly 24 enable the position of the distal tip to be tracked, once assembly 24 has been calibrated, in the magnetic system's frame of reference. (In some embodiments handle 62 may incorporate controls allowing the physician to control acquisition of the signals from sensor 32, when the distal tip touches the skin.) Processor correlates the distal tip positions in the magnetic system's frame of reference with the positions in the CT image frame of reference in order to register the two frames.

The Carto® system produced by Biosense Webster, of 31 Technology Drive, Irvine, Calif. 92618 USA, uses a system similar to that described herein for finding the location and orientation of a coil in a region irradiated by magnetic fields, and this system may be used for registration of the two frames. Alternatively, one or more other methods for registration, known in the art, may be used to perform the registration.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A surgical tool, comprising:
   (a) a handle;
   (b) a flexible insertion tube comprising:
      (i) a proximal end coupled to the handle, and
      (ii) a distal end configured to be inserted into an orifice of a body of a living subject;
   (c) an inner tube that is malleable between an initial shape and a bent shape without breaking over a range of angles from 0 to 120 degrees in response to application of a bending force, wherein the inner tube is configured to retain the bent shape after removal of the bending force, the inner tube being located within the insertion tube and having a distal termination in proximity to the distal end of the insertion tube, wherein the inner tube includes an outer surface;
   (d) a flexible tubing that defines a lumen, wherein the flexible tubing is contained within the inner tube;
   (e) a working tip that includes an opening and an outer surface, wherein the working tip is configured to contact tissue in the body and to mate with the distal termination of the inner tube; and
   (f) a rigid outer tube that holds at least a portion of the respective outer surfaces of the working tip and of the inner tube so as to maintain the opening of the working tip in communication with the flexible tubing lumen.

2. The surgical tool according to claim 1, further comprising at least one magnetic sensor located in proximity to the working tip.

3. The surgical tool according to claim 2, wherein the at least one magnetic sensor is configured to generate a signal, indicative of a location and an orientation of the working tip within the body, in response to a magnetic field traversing the at least one magnetic sensor.

4. The surgical tool according to claim 2, further comprising cabling, operatively coupled with the at least one magnetic sensor and configured to transfer signals therefrom, the cabling being located between the inner tube and the flexible insertion tube.

5. The surgical tool according to claim 2, wherein the magnetic sensor is disposed between the rigid outer tube and the working tip.

6. The surgical tool according to claim 2, wherein a cavity exists between the magnetic sensor and the rigid outer tube.

7. The surgical tool according to claim 2, wherein the magnetic sensor is coupled with the outer surface of the working tip.

8. The surgical tool according to claim 1, wherein the flexible insertion tube at least partially covers the outer tube.

9. The surgical tool according to claim 1, wherein the inner tube is formed from bendable aluminum.

10. The surgical tool according to claim 1, wherein the tool is operative as a suction tool.

11. The surgical tool according to claim 1, further comprising a camera positioned in the working tip and configured to image a section of the body external to the tip.

12. The surgical tool according to claim 11, wherein the working tip is formed as a rigid tubular element, and wherein the camera is located within the rigid tubular element.

13. The surgical tool according to claim 1, wherein the working tip defines a longitudinal axis, wherein the opening of the working tip extends at an angle relative to the longitudinal axis.

14. The surgical tool according to claim 1, wherein the rigid outer tube includes a proximal end, wherein the distal end of the flexible insertion tube surrounds a proximal end of the rigid outer tube.

15. A surgical tool, comprising:
   (a) a handle;
   (b) a flexible insertion tube comprising:
      (i) a proximal end coupled to the handle, and
      (ii) a distal end configured to be inserted into an orifice of a body of a living subject;
   (c) a malleable inner tube that is bendable between an initial shape and a bent shape without breaking over a range of angles from 0 to 120 degrees in response to application of a bending force, the inner tube being located within the insertion tube and having a distal termination in proximity to the distal end of the insertion tube;
   (d) a flexible tubing, which defines a lumen and which is contained within the inner tube;

(e) a working tip, which has an opening, and which is configured to contact tissue in the body and to mate with the distal termination of the inner tube; and (f) a rigid outer tube, which grips respective outer surfaces of each of the working tip and of the inner tube so as to maintain the opening of the working tip in communication with the flexible tubing lumen.

16. The surgical tool according to claim 15, wherein the working tip includes a lumen, wherein the lumens of the flexible tubing and the working tip collectively define a channel configured to carry fluid therethrough.

17. The surgical tool according to claim 15, wherein the magnetic sensor is disposed between the rigid outer tube and the working tip.

18. A surgical system, comprising:
(a) a magnetic radiator assembly that includes a plurality of magnetic field radiators, wherein the plurality of magnetic field radiators is configured to be arranged around a head of a living subject and configured to transmit magnetic fields into the head of the living subject; and
(b) a surgical tool comprising:
  (i) a handle,
  (ii) a flexible insertion tube comprising:
    (A) a proximal end coupled to the handle, and
    (B) a distal end configured to be inserted into an orifice of the head of a living subject,
  (iii) an inner tube that is malleable between an initial shape and a bent shape without breaking over a range of angles from 0 to 120 degrees in response to application of a bending force, wherein the inner tube is configured to retain the bent shape after removal of the bending force, the inner tube being located within the insertion tube and having a distal termination in proximity to the distal end of the insertion tube, wherein the inner tube includes an outer surface,
  (iv) a flexible tubing that defines a lumen, wherein the flexible tubing is contained within the inner tube,
  (v) a working tip that includes an opening and an outer surface, wherein the working tip is configured to contact tissue in the head and to mate with the distal termination of the inner tube,
  (vi) a rigid outer tube that captures at least a portion of the respective outer surfaces of the working tip and of the inner tube so as to maintain the opening of the working tip in communication with the flexible tubing lumen, and
  (vii) a magnetic sensor configured to generate a signal, indicative of a location and an orientation of the working tip within the head, in response to the magnetic field traversing the magnetic sensor.

19. The surgical system according to claim 18, wherein the plurality of magnetic field radiators are configured to be arranged in an approximately horseshoe shape around a head of the living subject.

20. The surgical system according to claim 18, wherein the magnetic sensor is disposed between the rigid outer tube and the working tip.

* * * * *